United States Patent [19]

Heather

[11] Patent Number: 4,625,065

[45] Date of Patent: Nov. 25, 1986

[54] PROCESS FOR PREPARATION OF TRIMETHYLSULFOXONIUM SALTS

[75] Inventor: James B. Heather, Hercules, Calif.

[73] Assignee: Stauffer Chemical Company, Westport, Conn.

[21] Appl. No.: 710,783

[22] Filed: Mar. 11, 1985

Related U.S. Application Data

[63] Continuation of Ser. No. 510,144, Jul. 1, 1983, abandoned.

[51] Int. Cl.$^4$ .............................................. C07C 161/00
[52] U.S. Cl. ................................... 568/27; 260/502.6; 260/505 R
[58] Field of Search ............... 568/27, 28; 260/505 R, 260/502.6

[56] References Cited

U.S. PATENT DOCUMENTS

| | | | |
|---|---|---|---|
| 2,870,163 | 1/1959 | Davis et al. | 568/27 |
| 3,534,105 | 10/1970 | Distler et al. | 568/27 |
| 4,141,920 | 2/1979 | Dryden, Jr. et al. | 568/27 |

OTHER PUBLICATIONS

N. Milas et al., J.A.C.S., 58, pp. 1302–1304, (1936).
J. Courtney et al., Rev. Pure Appl. Chem. 1972, 22 (Jun.), 47–54, Ruthenium Tetraoxide Oxidations.
R. Kuhn et al., Justus Liebig's Annalen der Chemie, v. 611: 117–21 (1958), Trimethyl-Sulfoxonium Ion.

*Primary Examiner*—Donald G. Daus
*Assistant Examiner*—Mary E. Ceperley
*Attorney, Agent, or Firm*—Paul R. Martin

[57] ABSTRACT

A method for the production of trimethylsulfoxonium salts is described in which trimethylsulfonium salts are oxidized with ruthenium tetraoxide in the presence of an inert solvent to form the corresponding trimethylsulfoxonium salts.

4 Claims, No Drawings

PROCESS FOR PREPARATION OF TRIMETHYLSULFOXONIUM SALTS

This is a continuation of application Ser. No. 510,144 now abandoned, filed July 1, 1983.

BACKGROUND OF THE INVENTION

The present invention relates to a process for the preparation of trimethylsulfoxonium salts. Trimethylsulfoxonium salts have a number of uses within the chemical industry, and are particularly useful when utilized as the trimethylsulfoxonium salt of N-phosphonomethylglycine which is an effective herbicide. The salts are not easy to produce. One method disclosed in the prior art, U.S. Pat. No. 3,534,105, involves reacting a sulfonium salt with aqueous hydrogen peroxide in the presence of an inert solvent at a temperature of from 20° to 100° C. Efforts to duplicate the process disclosed in that patent have not been successful. Another method of manufacture involves the reaction of dimethyl sulfoxide with methyl iodide, as described by R. Kuhn and H. Trischmann, Ann., 611, 11721 (1058). The disadvantage of this method is that it involves the use of expensive methyl iodide and the reaction is very slow. Still another method involves the reaction of dimethyl sulfoxide with methyl bromide, this reaction being described in U.S. Pat. No. 4,141,920. The disadvantage of this reaction is that it requires greater than atmospheric pressure, the reaction is slow, and explosions during the reaction have been reported. Consequently alternative methods of producing trimethylsulfoxonium salts are continually being sought. The present invention relates to one such alternative method of producing the salts.

DESCRIPTION OF THE INVENTION

It has now been discovered that trimethylsulfoxonium salts can be produced in good yields by the oxidation of trimethylsulfonium salts with ruthenium tetroxide (also known as ruthenium (VIII) oxide) in the presence of water or other inert solvent. The trimethylsulfonium salts used as starting compounds in the process of the instant invention have the general formula $(CH_3)_3S^+X^-$.

wherein X represents an anion selected from the group consisting of chloride, bromide, methosulfate, alkyl or aryl sulfonate wherein the alkyl group is from 1 to 10 carbon atoms and the aryl group is from 6 to 12 carbon atoms.

Ruthenium tetroxide is used in the process of the invention to oxidize the trimethylsulfonium salts. No other oxidant has been found to be suitable. The tetraoxide can be produced by any method and used alone in the process in stoichiometric amounts. Any source of a soluble, low valence ruthenium species can be used, however, the most convenient method to prepare it is to prepare it in situ in catalytic amounts from ruthenium dioxide hydrate or ruthenium [III] chloride with a suitable co-oxidant being present in stoichiometric amounts. The co-oxidant must be capable of oxidizing Ru from the III or IV to VIII oxidation states. Suitable co-oxidants are sodium periodate, sodium hypochlorite, and tertiary-butylhypochlorite, for example. In the process of the invention, the reaction of ruthenium tetroxide and the trimethylsulfonium salts regenerates ruthenium dioxide, which is then reoxidized to ruthenium tetroxide by the co-oxidant to continue the catalytic cycle.

The preferred trimethylsulfonium salt for use as starting material in the process of the invention is trimethylsulfonium chloride and when this preferred salt is used in conjunction with ruthenium tetroxide and co-oxidant sodium hypochlorite in water as solvent, the reaction can be represented as follows:

$(CH_3)_3S^+Cl^-$ + 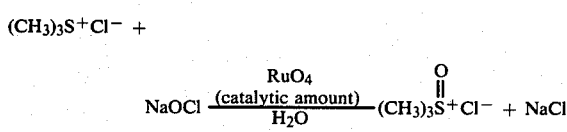

Another method of preparing the ruthenium tetroxide is to generate it from the reaction of ruthenium dioxide hydrate with sodium hypochlorite or any of the co-oxidants listed above.

While the amount of ruthenium tetroxide used must be sufficient to catalyze the reaction the exact amount is not critical.

The preferred inert solvent for use in the process of the invention is water, however other solvents such as organic solvents inert under the reaction conditions such as carbon tetrachloride or chloroform can also be used. The solvent is normally used in excess, although the exact amount is not critical. When organic solvents such as carbon tetrachloride are used, they are normally used in conjunction with water, forming an aqueous phase and an organic phase.

The instant process yields end product trimethylsulfoxonium salts in substantial quantities at a higher efficiency level than can be achieved by the methods of the prior art.

This invention will be more fully understood by reference to the following examples.

EXAMPLE I

Preparation of Trimethylsulfoxonium Chloride

A solution of 50% trimethylsulfonium chloride in water was prepared, and to 5 grams (g) of this solution was added 0.05 g of ruthenium dioxide hydrate and 10 milliliters (ml) of water. Thereafter, sodium metaperiodate (4.77 g) was added to the reaction mixture in portions over a period of several hours. A thick slurry of sodium iodate formed, and this mixture was filtered. The filtrate was analyzed by nuclear magnetic resonance (nmr) spectroscopy and was found to contain trimethylsulfoxonium chloride with only a trace (<2%) of unreacted trimethylsulfonium chloride. No other products were detected.

EXAMPLE II

Preparation of Trimethylsulfoxonium Chloride

A mixture of 5 g of trimethylsulfonium chloride, 3 g of water, and 3 mg of ruthenium dioxide hydrate was stirred under a chlorine atmosphere. A solution of sodium hypochlorite (11.5%) in water was added over 5.5 hours. The pH of the mixture remained below 7 throughout the reaction. The aqueous product mixture was extracted three times with chloroform to remove ruthenium tetroxide. Analysis of the product solution by nmr showed 78% conversion to trimethylsulfoxonium chloride.

The process of the invention is preferably carried out at a pH of between about 2 to about 7. Normally speaking, the incipient pH of the reaction mixture will be on the acidic side. When concentrated sodium hypochlorite is used as a co-oxidant, however, the reaction mixture becomes alkaline and in that instance the pH should be adjusted downward. The pH of the solution can be adjusted with an acid such as HCl to achieve the correct balance. The pH can also be adjusted by the use of a chlorine atmosphere over the reaction solution. The other co-oxidant reagents which can be used are more or less neutral and do not require the addition of acid. Even use of a low concentration hypochlorite solution (i.e., 5.25%) does not require an adjustment of the pH.

The reaction is preferably carried out at ambient temperature. The temperature is not critical, however.

In the practice of the process of this invention, it is convenient to generate sodium hypochlorite in situ by the addition of sodium hydroxide solution to the reaction mixture of the sulfonium salt, ruthenium catalyst, and water, with agitation under a chlorine atmosphere. Thus, pH is maintained below 7 as is required by the reaction, and the volume of water added to the reaction may be reduced.

Excess co-oxidant may be used to drive the reaction to completion.

It will be appreciated by those skilled in the art that variations in the amounts of constituents used, as well as temperature, and other reaction conditions, etc., can be made without departing from the spirit and scope of the invention as described herein.

What is claimed is:

1. A process for the preparation of trimethylsulfoxonium salts which consists essentially of reacting a trimethylsulfonium salt of the formula

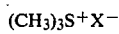

wherein X represents an anion, with a catalytic amount of a ruthenium tetraoxide oxidant prepared in situ from soluble, low valent ruthenium species with a stoichiometric amount of a suitable co-oxidant capable of oxidizing ruthenium from a III or IV to VIII oxidation state, selected from the group consisting of sodium periodate, sodium hypochorite and tertiary butyl hypochlorite, in the presence of an inert solvent at a temperature and for a sufficient period of time to cause formation of said trimethylsulfoxonium salt.

2. The process of claim 1 in which said trimethylsulfonium salt is trimethylsulfonium chloride.

3. The process of claim 1 wherein said co-oxidant is sodium periodate.

4. The process of claim 1 wherein said soluble, low valent ruthenium species is selected from ruthenium dioxide hydrate or ruthenium [III] chloride.

* * * * *